United States Patent [19]

Maslowski et al.

[11] 3,970,530
[45] July 20, 1976

[54] METHOD OF AND SYSTEM FOR THE DESTRUCTION AND/OR LIMITATION OF THE REPRODUCTION OF MICRO-ORGANISMS IN NUTRITIVE MEDIA

[75] Inventors: Bohdan Maslowski, Chene-Bougeries, Geneva; Dimitri Tzanos, Grand-Lancy, Geneva, both of Switzerland

[73] Assignee: Battelle Memorial Institute, Carouge, Geneva, Switzerland

[22] Filed: Aug. 6, 1974

[21] Appl. No.: 495,257

[30] Foreign Application Priority Data

Aug. 6, 1973   Switzerland.................... 11350/73

[52] U.S. Cl. ............................................. 426/237
[51] Int. Cl.² ........................................... A23B 7/00
[58] Field of Search................ 204/137 G; 426/237, 426/244

[56] References Cited
UNITED STATES PATENTS

1,850,594   3/1932   Matzka ........................ 204/137 G

OTHER PUBLICATIONS

"Dangerous Properties of Industrial Materials" by Sax, 3rd Ed. 1968 pp. 517, 903.

*Primary Examiner*—R. L. Andrews
*Attorney, Agent, or Firm*—Karl F. Ross; Herbert Dubno

[57] ABSTRACT

The reproduction, growth and multiplication of micro-organisms and their destruction in a nutritive medium which is electrically conductive is effected by introducing into the medium ions of at least one oligodynamic transition metal by providing on a roughened surface within a container for that medium a multiplicity of galvanic couples each including an anode of the transition metal and a cathode constituted by at least one metal having a standard oxidation potential lower than that of the transition metal. The surface is designed to provide a multiplicity of triple contact points between the anodic metal, the cathodic metal and the medium.

9 Claims, 2 Drawing Figures

METHOD OF AND SYSTEM FOR THE DESTRUCTION AND/OR LIMITATION OF THE REPRODUCTION OF MICRO-ORGANISMS IN NUTRITIVE MEDIA

FIELD OF THE INVENTION

The present invention relates to a process for the destruction of micro-organisms and/or for the inhibition of the growth of micro-organisms and/or for the prevention of multiplication (replication) or proliferation of micro-organisms in a conductive medium having nutritive properties with respect to the micro-organism. The term "micro-organism" as used herein is intended to refer to any microbial, bacterial or viral species, to fungus and to like parasites which are susceptible to static or cidal effects of oligodynamic metals.

BACKGROUND OF THE INVENTION

From research carried out in various laboratories, it is known that there is a significant proliferation of bacteria and like micro-organisms during storage periods in a medium which contains nutritive elements with respect to these micro-organisms. This is the case even if the medium does not contain originally any significant level of such micro-organisms.

The problem arises particularly in the case of mineral water stored in bottles and other viscous or fluid media found in containers and stocked for long periods by stores, warehouses and the like. Analysis of mineral water stored in bottles shows that the micro-organism content is at least 10 times greater for water stored in plastic bottles than for water stored in glass bottles. This is a result of the fact that the plastic bottles contain substances, as noted below, which provide a nutritive medium for micro-organisms and promote reproduction even where the water has been sterilized so that only miniscule quantities of the micro-organism may be present originally.

The problem is significant since the use of mineral water and other liquid beverages or the like in plastic bottles is constantly increasing.

While various bacterial species are commonly found in water stored in glass bottles, other species are found to develop in bottles of synthetic-resin materials. This demonstrates that the synthetic-resin material plays the role of a nutritive medium, probably because of the presence of substances of low molecular weight, such as plasticizers and lubricants, in the synthetic-resin material as required for fabrication of plastic bottles. Such substances are able to form, on the surface of a plastic bottle, linear chains which favor the development of bacteria or germs. It is also known that the proliferation of bacteria in plastic bottles for the storage of water is a function of the composition of the water itself, notably the level of its mineral salts.

While most of the micro-organisms have little effect, there is always the danger of a toxic condition developing since the micro-organisms may attain a level of $10^5$ or $10^6$ germs per $cm^3$. At these levels, the contaminated water is able to produce intestinal indisposition in children and adults.

Another example of a nutritive medium which may become contaiminated by micro-organisms is to be found in the cosmetic field.

As is known, cosmetic compositions are highly complex and especially so in comparison with table water. Generally such cosmetic compositions are emulsions having for the most part, a continuous aqueous phase and are not suitable subjects for sterilization techniques using thermal processes.

The protection of cosmetics by incorporating in them antiseptic substances is less than perfect. For example, the esters of parahydroxybenzoic acid cause allergic dermititis and irritation of the skin at doses which are sufficient to prevent proliferation of certan Gram-negative bacteria such as pseudomonas sp.

The latter germs are capable of metabolizing the antiseptic and diminishing its concentration, thereby promoting the development of other species of micro-organisms. The problem is complicated further by a supplemental pollution during the use of the cosmetic, i.e. from contact with the skin, which may be a source of infection.

It is well known that a sterilization process may consist of introducing ions of at least one transition metal, especially ions of silver ($Ag^+$), into water. Such processes utilize the bactericidal action which is well-known to be associated with certain transition metals, namely, the ions of the following metals: chromium, copper, zinc, cadmium, antimony and mercury.

This bactericidal action is generally described as an oligodynamic effect of the transistion metals. It is indeed surprising that relatively small quantities of such metals, particularly silver, may be used to sterilize water and yet create a system which is nontoxic to the human environment. Since silver and others of the oligodynamic metals mentioned previously form salts with contents of the digestive tract, they may be eliminated with food waste and do not tend to accumulate in the organism or, at most, accumulate only slightly.

In the case of silver, 15 to 30 grams of this substance in the human organism creates a disorder which has been denominated argyria, characterized by a blueish coloration of the skin and well known in the 19th century when curative doses of silver werre administered to patients for the treatment of certain nervous disorders. However, the amount of silver which accumulates in human organism is substantially below this toxic quantity when silver is used as a bactericidal agent in the treatment of water.

It has been calculated that a person drinking daily a liter of water containing 0.015 mg of silver per liter accumulates in his organism 3.75 g of the metal after 70 years. This quantity is significantly lower than the toxic quantities mentioned previously.

In order to introduce silver ions into water according to known sterilization processes as mentioned above, it is the general practice to bring the water into contact with pure silver in the metallic state. This may be done by immersing a plate or a wire of silver in water. Thus, where it is desired to sterilize water to be stored in a container, one need only provide a metallic silver layer along an internal wall of the vessel or as a coating on a projecting member reaching into the liquid.

In another sterilization process, the silver ions are produced by electrolytic solubilization of a silver electrode in water. For this purpose at least two electrodes of silver are generally provided.

While the latter techniques have been employed with success in the sterilization of water, especially in the case of sterilizing water for municipal distribution at reservoirs feeding municipal distribution lines and with flowing water in fisheries and the like, they have the significant disadvantage that it is not possible to bring sufficient silver into solution to inhibit proliferation of micro-organisms in the presence of a nutritive environment. In other words, the system is operable where nutrients are not present or are present in only extremely small concentrations, but has not been found to be successful in systems which can be considered nutrient media.

Thus with respect to stored water (e.g. mineral water) in plastic vessels, fruit juices, vegetable soup and the like which have high nutrient value for microorganisms, it is not possible to provide by the aforementioned techniques a sufficiently high level or concentration of silver to ensure continued bactericidal action.

Thus the usual approach to such nutritive systems has been the use of thermal sterilization or the like, techniques which are not suitable for completely effective sterilization for the aforementioned products.

Cosmetics, in the form of liquids or pastes, constitute a prime example of systems which cannot be readily sterilized by conventional techniques including those in which the silver concentration is raised by contact of the liquid phase with a pure silver wire. These systems contain nutritive components which give rise to a high rate of proliferation of the micro-organisms so that inhibition of such proliferation is a great problem. In fact, such cosmetics had to be manufactured heretofore in highly aseptic conditions and must be stored aseptically in their receptacles. However, once the cosmetic receptacle is opened, all hope of maintaining a sterile condition must fail. Inevitably, the repeated opening and closing results in an inoculation of the medium with microbial species present in the atmosphere, on the skin of the user, or upon the walls of the environment in which the cosmetic is stored or used.

OBJECTS OF THE INVENTION

It is the principal object of the present invention to provide a process and a system for not only destroying micro-organisms but also inhibiting their proliferation in an electrolytically conductive medium which has nutritive characteristics with respect to the microorganisms.

It is another object of the invention to provide a method of and a system for preventing the proliferation of micro-organisms in nutritive media stored in receptacles.

Still another object of the invention is to provide a method of and a system for the sterilization of mineral water stored in plastic bottles, and of cosmetics constituting nutritive media, and, also, to provide a technique for destroying bacteria and like microbial species which tend to proliferate in such media.

SUMMARY OF THE INVENTION

These objects and others which will become apparent hereinafter are attained, in accordance with the present invention, by maintaining the nutritive electrically conductive medium in contact with a multiplicity of galvanic couples spread over a rough surface, each couple consisting of an anode of a transition metal of the oligodynamic type and a cathode constituted by a metal having a standard oxidation potential less than that of the transition metal, the surface forming a multiplicity of triple-contact points between the anodic metal, the cathodic metal and the electrically conductive medium.

Thanks to the roughness of the structure, it has been found to have high surface activity and the oligodynamic germicidal effect of the transition metal is accelerated, the transition metal being liberated progressively in a substantially uniform and continuous manner over long periods of time by the galvanic action. Since fresh transition-metal ions are continuously being released into the medium, the ability to destroy micro-organisms which are present and are produced and to inhibit their proliferation is increased. The action of the ions is therefore continuous as long as the galvanic action continues and is effective to destroy both micro-organisms which are originally present and those which are introduced from time to time into the medium. Moreover, there is the advantage that it is not necessary to introduce initially a high concentration of the oligodynamic-metal ions because such ions are continuously released.

Preferably the surface roughness is such that $H_{max}$, i.e. the maximum height of the peaks of the surface, as measured from any depressions therein, is equal to 50 to 2000 microns. The surface may be pitted so that, where concavities are formed, the concavities have a length and width of the order of 50 to 2000 microns as well. Thus, we can define a mean cavity size of 50 to 2000 microns for all the dimensions (height, width and length). The ratio between the effective surface area and the geometric surface area of the support preferably lies between 2 and 5.

The galvanic surface can be prepared according to the invention in one of several ways.

Each of a multiplicity of composite granules, which can be adhered together or used as distinct pellets or agglomerates, is formed from a grain of the transition metal, especially silver, having dimensions of the order of 200 to 500 microns, on the surface of which are fixed a multiplicity of grains of a more noble metal (for example gold or platinum) having a standard oxidation potential substantially lower than that of the transition metal. The latter grains have, for example, dimensions between 20 and 100 microns.

Advantageously, the metal grains utilized for the production of such granules have spheroidal form and any method may be used to adhere the grains of the more noble (cathodic) metal to the surface of the grains of the transition (avodic) metal. For example, it is possible to cause such adhesion by applying mechanical pressure at ambient temperature or by pressure with heating (sintering) or even by sintering under atmosphere pressure.

Another way of forming the roughened surface with triple-contact points, at which the medium is in contact with a junction between the anodic and cathodic metals is to deposit a layer of the transition metal (in a thickness of about 2 to 15 microns) simultaneously with granules of the more noble metal on a pitted substrate potential. These granules can have dimensions of the order of 20 to 150 microns. The substrate may be, for example, a plate of fritted glass, a screen, net or latticework of synthetic-resin material or a metal. When a plastic or metal screen is used, it should have a fine mesh so that the openings have a width of 50 to 2000 microns.

The rough-surfaced substrate upon which the metals are deposited can be part of a wall of the container in which the medium is to be stored or can be introduced into the container concurrently with, prior to or after the medium.

The electrochemical action commences when the medium contacts both the transition metal serving as the anode and the more noble metal constituting the cathode.

The electrochemical mechanism thus is similar to the effect of a "micropile" which is produced by placing the two metals in contact with an electrically conductive medium, thereby effecting reduction at the cathode while the transition metal forming the anode is gradually solubilized. The reduction phenomenon is accompanied by the evolution of hydrogen.

The micropile effect between two or more metals is a consequence of the heterogeneous character of the reaction surface which is a function of:

surface roughness;

the presence of at least one more noble metal in a more or less continuous layer of the transition metal; and partial oxidation of this surface.

When it is desirable to inhibit proliferation of microbial species in a medium constituting a comestible, for example a beverage such as mineral water, or in a medium destined to come into contact with the skin of a person, for example a cosmetic product, it is essential that the ions released into solution are not those of a toxic metal. We have found that it is best to use silver as the transition metal since silver has a highly oligodynamic effect and is largely removed from the digestive system by precipitation in the eliminated wastes of the body.

A nontoxic noble metal used together with silver may be gold or platinum. The silver ions are progressively and continuously liberated by means of the "pile" effect mentioned above.

We prefer, as a practical matter, to use platinum as the cathode metal because the overvoltage of hydrogen on platinum is significantly lower than that on gold, thereby promoting the pile effect.

It has been found that the rate at which silver goes into solution in ionic form, because of the galvanic action mentioned above, depends also upon the pH of the medium and is greater in an acid or in a neutral medium than in a basic medium. Preferably the present invention is carried out in a medium with a pH between 5 and 7 and we may adjust the pH of the orginal medium, if necessary, to this range by adding acidic substances or buffer systems.

The oligodynamic effect of ions of the transition metals mentioned above depends upon the nature and form of the complex between the ion and the plasma of the micro-organism. In fact, certain metal ions are capable of combining with functional groups of the proteins participating in the metabolic operations of the micro-organisms to produce a change in their structure, e.g. to form agglomerates having a size of the order of 1000 to 1500 A. This action is a result of covalent bonding or coordination between the metabolic species of the micro-organism and the metal ion.

The association of a protein group with the metal ion may also depend upon the ionization state of the metal. This association mechanism is regulated by the competition between the hydrogen ions liberated at the cathode and the metal ions liberated at the anode.

The practical application of the invention to a closed vessel or container may take various forms. For example, one may apply metallic silver in admixture with particles of the more noble metal along the inner wall of the receptacle to provide a pattern on the receptacle wall for publicity or other purposes, especially where the container wall is transparent.

A plug or other insert, which projects into the medium, may be formed. Tablets, disks or the like of the two metals formed by compression or sintering may be simply introduced into the vessel or suspended in a viscous medium therein. Of course, the metal may be applied by any metallization process to a surface of the container designed to contact the medium. Vacuum deposition, metallization by reduction and electrolysis techniques may be used.

While we have referred repeatedly herein to the use of silver or some other transition metal to form the anode of the electrochemical couple, it should be noted that the anode may also be constituted by an alloy of silver or a different transition metal with another element. Of course, it is not necessary to employ only two dissimilar metals to form the minipile of the present invention and indeed three or more elements which are interreactive in an electrochemical sense may be used. A typical electrode of the secondary type which can be effective according to the present invention makes use of the silver-chlorine couple $Ag/AgCl/Cl^-$. Such a system may be made by precipitating silver simultaneously with silver chloride and using, for example, gold as the cathode metal. An appropriate alloy for use as the anode material may be an alloy of silver with copper, bismuth or lead. A silver-lead alloy having 90% by weight silver may be used and the anodic current density is of the order of 30 milliamperes per centimeter square ($mA/cm^2$).

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
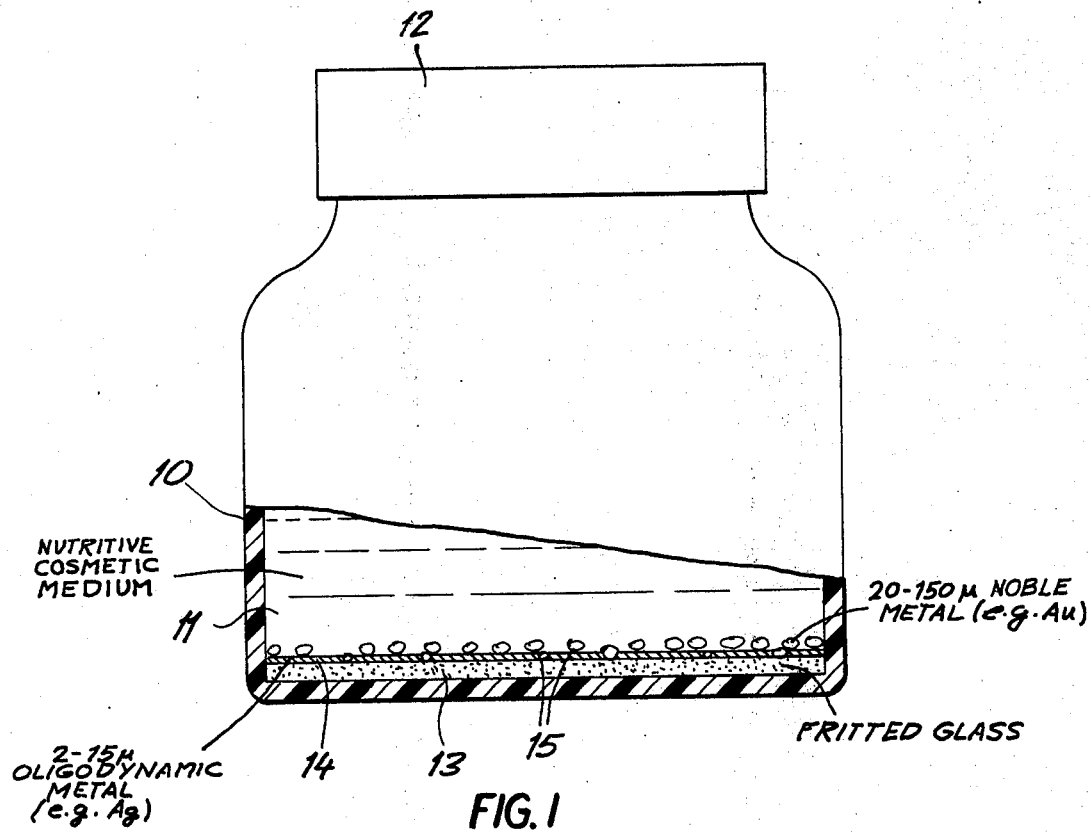
FIG. 1 is an elevational view, partly broken away, illustrating a cosmetic jar provided with a system according to the present invention.

In FIG. 1 of the drawing, we have shown a conventional jar 10 of synthetic resin containing a pasty cosmetic preparation 11 which can be considered electrolytically conductive and a nutritive medium with respect to bacterial or other micro-organisms. The jar is tightly sealed by cap 12 and, according to the invention, is provided with a disk 13 of fritted glass (during fabrication of the jar) carrying a layer 14 of silver co-precipitated with particles 15 of gold. The silver layer 14 may have a thickness of 2 to 15 microns while the particles of gold may have a particle size of 20 to 150 microns. The contact points between the gold, silver and medium are triple junctions sustaning the described electrolytic operation which releases silver into the system.

Figure 2:
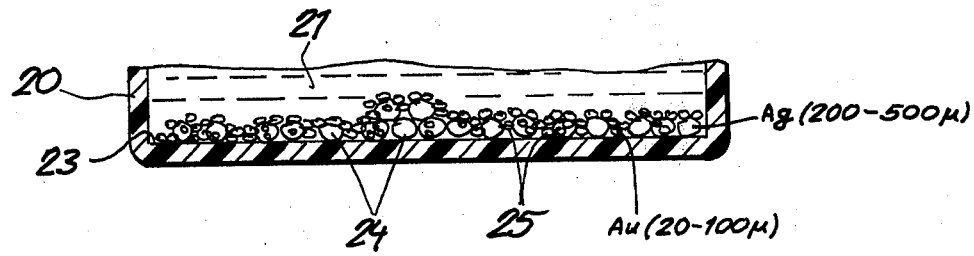
FIG. 2 is a fragmentary cross-section view of a plastic bottle for the storage of mineral water.

The plastic bottle 20 of FIG. 2 is provided on a rough bottom surface 23 with a layer of large silver particles 24 substantially in contact with one another and having small particles 25 of gold sintered thereto. The mineral water 21 of this system is electrolytically conductive as noted previously and may be considered a nutritive medium for micro-organisms.

Specific Examples

Example I

A layer of finely divided silver having a thickness of the order of 2 microns, and in which is distributed powdered gold with a particle size of 30 microns, is disposed on a fritted-glass plate having a thickness of 1 mm.

The plate has a porosity number of 0 (equivalent diameter of the pores equals 150 to 200 microns), a geometric surface area of 10 cm$^2$ (two surfaces of 3.33 × 1.5 cm), an effective surface (determined by the superficial roughness) of about 40 cm$^2$, and surface cavities of a mean size (as defined above) of about 150 microns.

The deposit of the metal is effected by chemical reduction of a solution of a silver salt, with agitation, after cleaning of the surface of the plate of fritted glass by a mixture of sulfuric acid and nitric acid.

Three solutions are prepared:

SOLUTION A

| | | |
|---|---|---|
| SnCl$_2$ | = | 30 grams |
| HCl | = | 30 grams |
| Deionized distilled water | = | q.v. 1000 ml. |

SOLUTION B

| | | |
|---|---|---|
| Silver nitrate | = | 2 grams |
| Potassium hydroxide | = | 1 gram |
| H$_2$O | = | 40 ml |
| Aqueous ammonia containing 25% by weight NH$_3$ | = | about 5 milliliters, as required to clear the solution |

SOLUTION C (for reduction)

| | | |
|---|---|---|
| Saccharose | = | 90 grams |
| Concentrated nitric acid | = | 4 milliliters |
| Distilled water | = | as necessary to complete 1000 milliliters |

The fritted glass plate is immersed in a bath of Solution A for a period of 3 months at a temperature of 20°C and then is rinsed with deionized water.

A bath comprising a suspension of gold powder (granulometry about 20 microns) is prepared from a silver solution consisting of four volumes of Solution B and one volume of Solution C and the plate is immersed in this bath for 20 minutes. The plate is then washed with deionized water' and is dried in air.

The plate is then found to be coated on both faces with a layer of siver having a thickness of the order of 2 microns and containing particles of gold partially occluded therein. The ratio, calculated by gravimetry, between the weight of gold fixed to the plate and the layer of silver is of the order of 0.1.

The plate is introduced into a plastic bottle which is filled with nongaseous mineral water previously inoculated with a minute quantity of bacteria (10$^6$ germs per gram of Gram-negative bacteria) for experimental purposes, whereupon the bottle is hermetically sealed. After about 30 days of storage at ambient temperature (about 20°C) a test shows that the water contains no more than 10$^2$ virulent germs per gram. This corresponds to a bactericidal effect of 4 orders of magnitude or at least 4 logarithmic cycles.

During this period it is observed that there is a progressive release of Ag$^+$ ions in the mineral water, a release corresponding to about 0.13 ppm of silver per day; the total over 30 days of storage is about four ppm.

EXAMPLE II

Proceeding as in Example I, but using in place of mineral water 100 grams of pure orange juice, without added sugar and with a fritted glass plate having the following characteristics:

| | | |
|---|---|---|
| Porosity | = | No. 0 |
| Geometric surface | = | 15 cm$^2$ |
| Effective surface | = | about 60 cm$^2$ |
| Mean size of superficial cavities | = | about 500 microns |

It is possible to obtain a bactericidal effect equivalent to at least 4 logarithmic cycles at the end of 30 days of storage at 20°C thanks to the liberation of Ag$^+$ ions in a quantity corresponding to about 0.33 ppm per day. The total quantity of liberated silver in solution after 30 days is about 10 ppm.

EXAMPLE III

The proceeding is carried out as in Example I except that 100 grams of a cosmetic emulsion having an aqueous continuous phase are used and the fritted glass plate has the following characteristics:

| | | |
|---|---|---|
| Porosity | = | 0 |
| Geometric surface | = | 10 cm$^2$ |
| Effective surface | = | about 20 cm$^2$ |
| Mean size of superficial cavities | = | about 350 microns |

A destructive effect of more than 4 logarithmic cycles is obtained at the end of 30 days of storage at 20°C. Silver ion is liberated at a rate of 0.25 ppm per day or a total quantity over 30 days of about 8 ppm.

EXAMPLE IV

The process is analogous to that of Example I with 100 grams of a cosmetic substituted for the mineral water, the cosmetic consisting of an emulsion having an oil continuous phase. The glass plaque has the following characteristics:

| | | |
|---|---|---|
| Porosity | = | No. 0 |
| Geometric surface | = | 10 cm$^2$ |
| Effective surface | = | 80 cm$^2$ |
| Mean size of superficial cavities | = | about 2000 microns |

The bactericidal effect is greater than 4 logarithmic cycles at the end of about 30 days storage. The quantity of Ag$^+$ ion released over 30 days is about 15 ppm, corresponding to a rate of about 0.5 ppm per day.

EXAMPLE V

The procedure is as in Example III but using an inoculation of the cosmetic of 10$^3$ germs per gram instead of 10$^6$ germs per gram. At the end of two years of storage at 20°C the bactericidal effect is equivalent to 3 to 5 logarithmic cycles. The silver is released at an estimated rate of 0.2 ppm per day for a total quantity liberated in two years of the order of 15 ppm.

The system of the present invention has been found to be particularly useful for protecting any electrically conductive medium susceptible to degradation by biological action, especially comestibles such as mineral water stored in receptacles of synthetic-resin material, fruit juices, wine, etc.

It is also especially effective for cosmetic products, particularly those in the form of an emulsion with continuous aqueous or oil phases, other pharmaceutical products and the emulsions customary for household use.

We claim:

1. A method of checking the growth of micro-organisms in an electrically conductive medium contaning nutrients conductive to the proliferation of such micro-organisms, comprising the steps of:
    placing said medium in a container for prolonged storage; and
    contacting said medium in said container with an anodic and a cathodic material constituting electrical couples for the autosolubilization in said medium of an oligodynamic transistion metal forming part of said anodic material, said cathodic material consisting of at least one metal more noble than said oligodynamic metal, said anodic and cathodic materials adhering to a rough surface of a substrate with a multiplicity of cavities whose mean size in all dimensions lies in a range of 50 to 2000 microns, said surface forming a multiplicity of triple-contact points between said anodic material, said cathodic material and said medium, at least one of said materials being in granular form.

2. The method defined in claim 1 wherein said oligodynamic metal is silver.

3. The method defined in claim 1 wherein said more noble metal is selected from the group which consists of gold and platinum.

4. The method defined in claim 1 wherein said anodic material is silver alloyed with at least one metal selected from the group which consists of copper, bismuth and lead.

5. The method defined in claim 1 wherein said anodic material is a silver-lead alloy containing 90% by weight silver.

6. A package for the prolonged storage without spoilage of an electrically conductive medium containing nutrients conducive to the proliferation of micro-organisms, comprising:
    a container filled with said medium;
    a solid substrate in said container having a rough surface with a multiplicity of cavities whose mean size in all dimension lies in a range of 50 to 2000 microns;
    an anodic material consisting of at least one oligodynamic transition metal on said surface; and
    a cathodic material consisting of at least one metal more noble than said oligodynamic metal adhering to said surface, said anodic and cathodic materials constituting electrical couples for the autosolubilization of said oligodynamic metal in said medium, at least one of said materials being in granular form, said surface forming a multiplicity of triple-contact points between said anodic material, said cathodic material and said medium.

7. A package as defined in claim 6 wherein said substrate is a fritted glass plate.

8. A package as defined in claim 6 wherein said substrae is an integral part of said container.

9. A package as defined in claim 6 wherein said anodic material forms a thin layer on said rough surface.

* * * * *

Dedication 3,970,530.—*Bohdan Maslowski; Dimitri Tzanos,* Geneva, Switzerland. METHOD OF AND SYSTEM FOR THE DESTRUCTION AND/OR LIMITATION OF THE REPRODUCTION OF MICRO-ORGANISMS IN NUTRITIVE MEDIA. Patent dated July 20, 1976. Dedication filed Mar. 26, 1984, by the assignee, *Battelle Memorial Institute.*

Hereby dedicates to the People of the United States the entire remaining term of said patent.

*[Official Gazette May 22, 1984.]*